United States Patent
Lee et al.

(10) Patent No.: US 9,895,624 B2
(45) Date of Patent: *Feb. 20, 2018

(54) DISTILLATION DEVICE

(71) Applicant: LG CHEM, LTD., Seoul (KR)

(72) Inventors: Sung Kyu Lee, Daejeon (KR); Joon Ho Shin, Daejeon (KR); Sung Kyun Kim, Daejeon (KR); Jong Ku Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/905,640

(22) PCT Filed: Jul. 18, 2014

(86) PCT No.: PCT/KR2014/006575
§ 371 (c)(1),
(2) Date: Jan. 15, 2016

(87) PCT Pub. No.: WO2015/009118
PCT Pub. Date: Jan. 22, 2015

(65) Prior Publication Data
US 2016/0158667 A1  Jun. 9, 2016

(30) Foreign Application Priority Data

Jul. 18, 2013 (KR) .................. 10-2013-0084495
Jul. 18, 2013 (KR) .................. 10-2013-0084496
(Continued)

(51) Int. Cl.
*B01D 3/14* (2006.01)
*B01D 3/00* (2006.01)
(Continued)

(52) U.S. Cl.
CPC .............. *B01D 3/141* (2013.01); *B01D 3/008* (2013.01); *B01D 3/143* (2013.01); *B01D 3/32* (2013.01);
(Continued)

(58) Field of Classification Search
CPC .......... B01D 3/14; B01D 3/141; B01D 3/143; B01D 1/007; B01D 3/008; B01D 3/32;
(Continued)

(56) References Cited

U.S. PATENT DOCUMENTS 2,081,601 A * 5/1937 Ridgway .............. B01D 3/4261
196/132
4,559,108 A * 12/1985 Ahlberg ............... B01D 1/2806
202/154
(Continued)

FOREIGN PATENT DOCUMENTS

CN  1227132 A   9/1999
CN  1678600 A   10/2005
(Continued)

*Primary Examiner* — Jonathan Miller
*Assistant Examiner* — Jonathan Luke Pilcher
(74) *Attorney, Agent, or Firm* — Dentons US LLP

(57) ABSTRACT

The present application relates to a distillation device and a distillation method, and according to the distillation device and method of the present application, channeling occurring during the separation of a mixture may be blocked, thereby enhancing the separation efficiency and achieving energy saving.

20 Claims, 6 Drawing Sheets

(30) Foreign Application Priority Data

Sep. 5, 2013 (KR) ........................ 10-2013-0106471
Jul. 18, 2014 (KR) ........................ 10-2014-0091355

(51) Int. Cl.
    *B01D 3/32*     (2006.01)
    *C07C 67/54*     (2006.01)
    *C07C 41/42*     (2006.01)

(52) U.S. Cl.
    CPC ................ *C07C 67/54* (2013.01); *B01D 3/14* (2013.01); *C07C 41/42* (2013.01)

(58) Field of Classification Search
    CPC .......... B01D 3/36; B01D 3/40; B01D 3/4261; B01D 3/322; B01D 3/20; B01D 3/4283; C07C 41/42; C07C 67/54; C07C 69/54
    USPC ......................................................... 203/84
    See application file for complete search history.

(56) References Cited

U.S. PATENT DOCUMENTS 6,294,056 B1 * 9/2001 Matsumoto ............ B01D 3/008 202/158

2005/0250965 A1 * 11/2005 Bassler ................... B01D 3/141 568/868
2016/0193540 A1 * 7/2016 Lee ......................... B01D 3/008 203/22
2016/0193541 A1 * 7/2016 Lee ......................... B01D 3/008 203/81

FOREIGN PATENT DOCUMENTS

| | | |
|---|---|---|
| CN | 101607908 A | 12/2009 |
| CN | 102188831 A | 9/2011 |
| CN | 102190559 A | 9/2011 |
| CN | 102281931 A | 12/2011 |
| CN | 101798528 B | 2/2013 |
| EP | 2457630 A2 | 5/2012 |
| EP | 2380645 B1 | 5/2014 |
| JP | 11-226301 A | 8/1999 |
| JP | 2004-300139 A | 10/2004 |
| JP | 2005-000860 A | 1/2005 |
| JP | 2005-104932 A | 4/2005 |
| JP | 2012-533424 A | 12/2012 |
| JP | 2013-525097 A | 6/2013 |
| KR | 10-2012-0076193 A | 7/2012 |

* cited by examiner

[Fig 1]
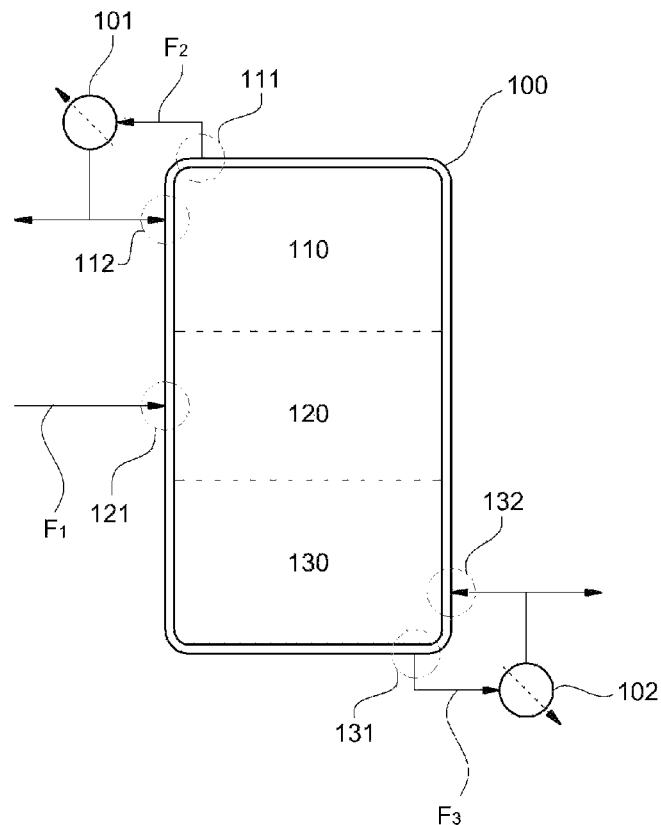
[Fig 2]
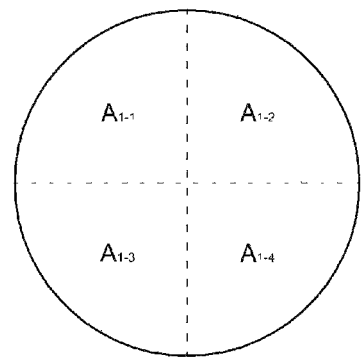

[Fig 3]
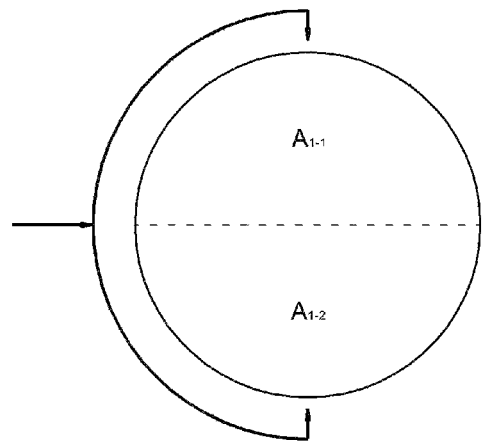
[Fig 4]
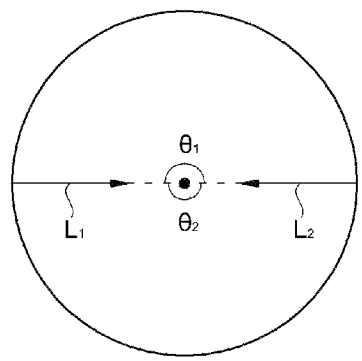
[Fig 5]
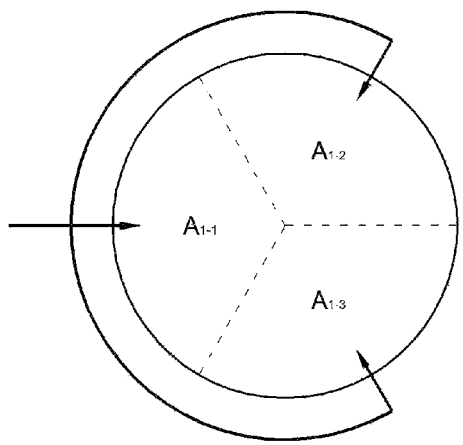

[Fig 6]
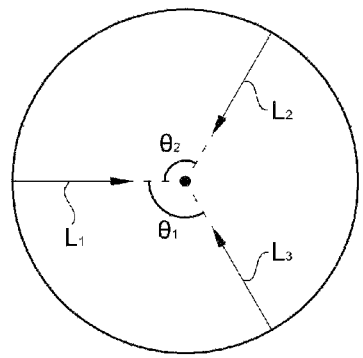
[Fig 7]
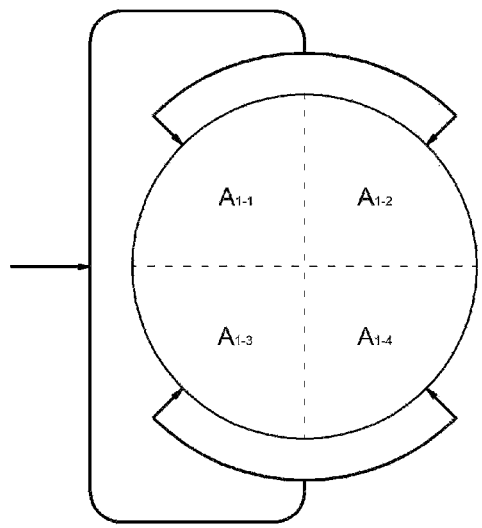
[Fig 8]
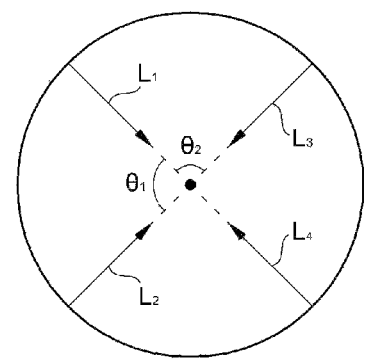

[Fig 9]
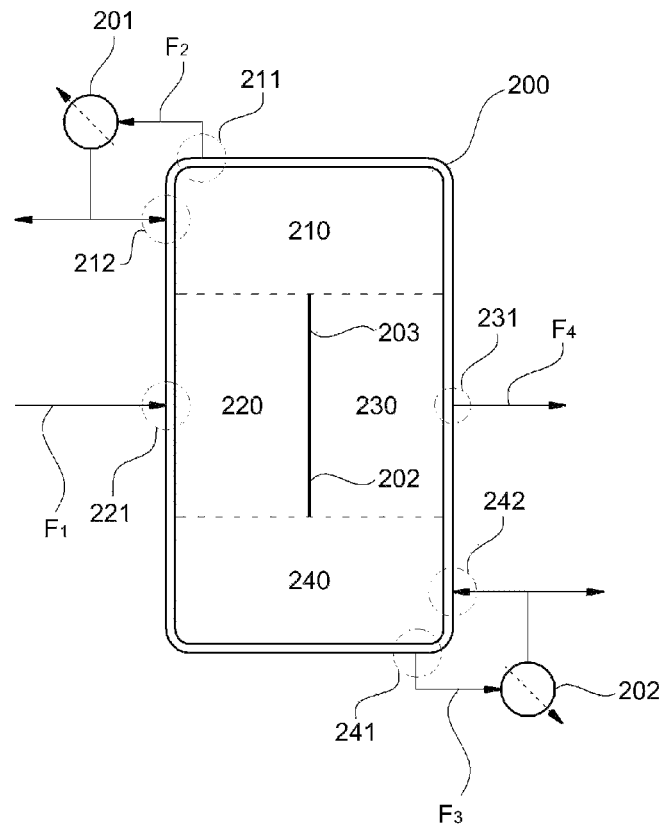
[Fig 10]
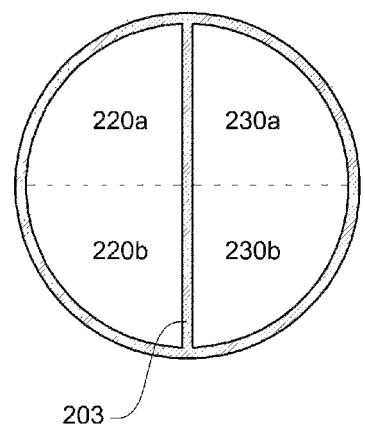

[Fig 11]
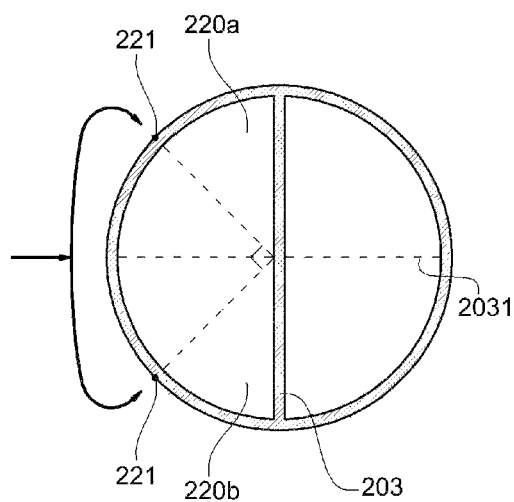
[Fig 12]
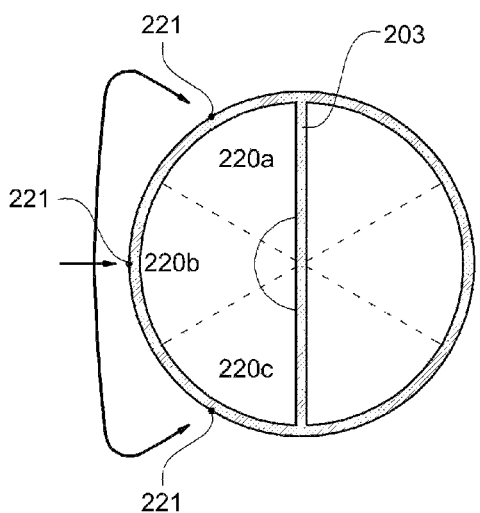

[Fig 13]
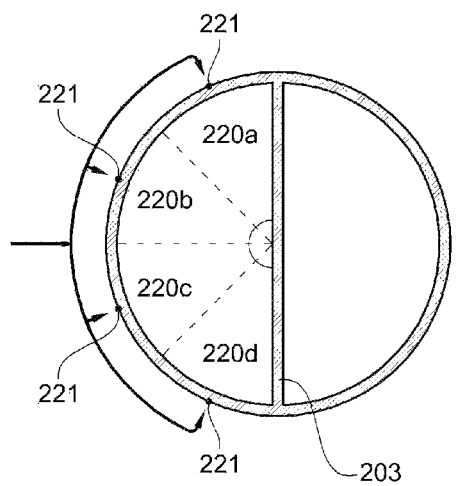
[Fig 14]
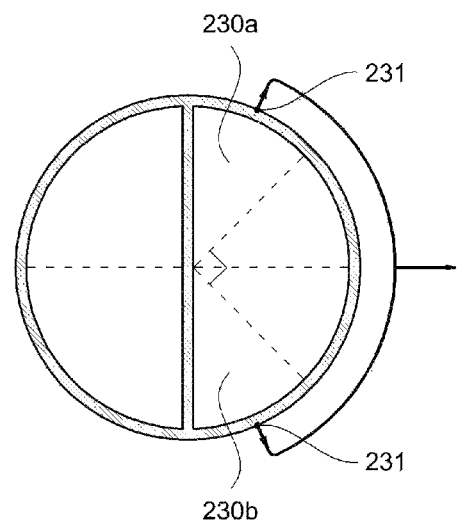

DISTILLATION DEVICE

This application is a National Stage Application of International Application No. PCT/KR2014/006575, filed on Jul. 18, 2014, which claims the benefit of Korean Patent Application No. 10-2013-0084495, filed on Jul. 18, 2013, Korean Patent Application No. 10-2013-0084496, filed on Jul. 18, 2013, Korean Patent Application No. 10-2013-0106471, filed on Sep. 5, 2013, and Korean Patent Application No. 10-2014-0091355, filed on Jul. 18, 2014, all of which are hereby incorporated by reference in their entirety for all purposes as if fully set forth herein.

TECHNICAL FIELD

The present application relates to a distillation device.

BACKGROUND ART

Various raw materials such as crude oil are mixtures of various materials, for example, various compounds, and the raw materials may be usually used after being separated into each compound. A representative process from among chemical processes for separating the mixture is a distillation process.

For example, the mixture may pass through one or more distillation columns and be distilled, a part or all of the stream in the distillation process may pass through a condenser or a reboiler, and then flow back to the distillation column, and a high-purity compound may be obtained through the process. It is common that in the case of a typical distillation column, a raw material or reflux stream is introduced in one direction, or a product stream also flows out in one direction only. However, when a raw material to be introduced into the distillation column is supplied in one direction only, a liquid to drop onto the lower part area of plates into which the raw material is introduced does not evenly drop, so that channeling may occur. Further, the liquid likewise drops unevenly even when the stream discharged from the distillation column flows back in one direction. In this case, unnecessary energy may be consumed in order to maintain the concentration of each stream.

DETAILED DESCRIPTION OF THE INVENTION

Technical Problem

An object of the present application is to provide a distillation device which may prevent channeling from occurring, and a distillation method using the same.

Technical Solution

The present application relates to a distillation device. In an exemplary embodiment of the distillation device, one or more of the inflow parts of the distillation device is formed of two or more openings disposed to be separated from each other. Accordingly, channeling occurring during the purification process of raw materials may be blocked, thereby minimizing energy loss and enhancing the economic efficiency of the process. The term "channeling" in the present specification refers to a phenomenon in which contact of a mixture of steam and liquid in a distillation column does not smoothly occur, or a liquid inclination phenomenon in which a fluid flows lopsidedly toward a specific part of a wall surface of a dividing wall distillation column, and channeling is responsible for a significant deterioration in efficiency of separating raw materials and additional energy consumption.

Hereinafter, the distillation device of the present application will be described with reference to drawings, but the drawings are illustrative only, and the scope of the distillation device is not limited thereto.

FIG. 1 is a view exemplarily illustrating a distillation device according to exemplary embodiments of the present application.

As illustrated in FIG. 1, the distillation device may include a distillation column 100 including a condenser 101 and a reboiler 102. The distillation column is a device which can separate a multi-component material included in a raw material ($F_1$) into each component using the difference in boiling points among the components, and distillation device having various forms may be used in the present application in consideration of boiling points and the like of components of the raw material ($F_1$) to be introduced or components to be separated and the like. For example, in the distillation device of the present application, a raw material including a mixture of three components of low boiling point, intermediate boiling point, and high boiling point materials may be separated by introducing the raw material into the distillation column 100. In the present application, the specific kind of distillation device which may be used during the process of distilling a mixture is not particularly limited, and for example, it is possible to use a distillation device including a distillation column 100 having a general structure as illustrated in FIG. 1.

As illustrated in FIG. 1, an exemplary distillation device of the present application includes the distillation column 100 including the condenser 101 and the reboiler 102. Further, the inside of the distillation column 100 may be divided into an upper plate 110, a lower plate 130, and a middle plate 120, or into an upper part 110, a lower part 130, and a middle part 120. The term "upper plate" or "upper part" in the present specification refers to a relatively upper part in the structure of the distillation column 100, and may refer to, for example, the upper part of the two areas obtained by dividing the distillation column 100 into two parts in a height or longitudinal direction of the distillation column. Further, the term "lower plate" or "lower part" described above refers to a relatively lower part in the structure of the distillation column 100, and may refer to, for example, the lower part of the two areas obtained by dividing the distillation column 100 into two parts in a height or longitudinal direction of the distillation column. In addition, the term "middle plate" or "middle part" in the present specification may refer to a middle area of the three areas obtained by dividing the distillation column 100 into three parts in a height or longitudinal direction of the distillation column, and may refer to an area between the upper part and the lower part of the distillation column 100. In the present specification, the upper part, the lower part, and the middle part of the distillation column 100 may be used as relative concepts to each other.

Furthermore, the term "condenser" used in the present specification may refer to, as a device disposed separately from the distillation column, a device for cooling by bringing a material discharged from the main body in contact with cooling water which flows in from the outside and the like. For example, the condenser 101 of the distillation device may be a device which condenses an upper product outflow stream ($F_2$) to be discharged from an upper plate outflow part 111 of the distillation column 100. Further, the term "reboiler" may refer to a device for re-boiling and evaporating a stream having a high boiling point as a heating device disposed outside of the distillation column. For example, the reboiler 102 of the distillation device may be a device which heats a lower product outflow stream ($F_3$) to be discharged from a lower plate outflow part 131 of the distillation column 100.

In an example, the distillation column 100 includes a raw material inflow part 121 to which the raw material ($F_1$) is supplied, the upper plate outflow part 111 from which a low boiling point stream is discharged, an upper reflux inflow part 112 into which a reflux flow of the flow discharged from the upper part 110 is introduced, the lower plate outflow part 131 from which a high-boiling point stream is discharged from the lower part 130 of the distillation column, and a lower reflux inflow part 132 into which a reflux flow of the flow discharged from the lower part 130 of the distillation column is introduced. For example, when the raw material ($F_1$) is introduced into the raw material inflow part 121 disposed at the middle plate of the distillation column 100, the introduced raw material ($F_1$) may be discharged while being divided into the upper product outflow stream ($F_2$) discharged from the upper plate outflow part 111 disposed at the upper part or upper plate 110 of the distillation column 100 and the lower product outflow stream ($F_3$) discharged from the lower plate outflow part 131 disposed at the lower part or lower plate 130 of the distillation column 100, respectively. The upper product outflow stream ($F_2$) discharged from the upper plate outflow part 111 passes through the condenser 101, and a part or all of the upper product outflow stream ($F_2$) which has passed through the condenser 101 may be introduced into the upper reflux inflow part 112 and flow back to the distillation column 100 or be stored as a product. Further, the lower product outflow stream ($F_3$) discharged from the lower plate outflow part 131 of the distillation column 100 passes through the reboiler 102, and a part or all of the lower product outflow stream ($F_3$) which has passed through the reboiler 102 may be introduced into the lower reflux inflow part 132 and flow back to the distillation column 100 or be stored as a product.

The term "low boiling point stream" in the present specification refers to a stream which is rich in a component having a relatively low boiling point in a raw material flow including three components having a low boiling point, an intermediate boiling point, and a high boiling point, and the low boiling point stream refers to, for example, a stream discharged from the upper plate outflow part 111 of the distillation column 100. The "high boiling point stream" in the present specification refers to a stream which is rich in a component having a relatively high boiling point in a raw material stream including three components having a low boiling point, an intermediate boiling point, and a high boiling point, and the high boiling point stream refers to, for example, a flow which is rich in a component having a relatively high boiling point discharged from the lower plate outflow part 131 of the distillation column 100. The term "stream which is rich" refers to a flow having a higher content of each of a low boiling point component included in the flow discharged from the upper plate outflow part 111 and a high boiling point component included in the stream discharged from the lower plate outflow part 131 than a content of each of the low boiling point component and the high boiling point component included in the raw material ($F_1$). For example, the term may refer to a stream in which each content of the low boiling point component included in the upper product outflow stream ($F_2$) and the high boiling point component included in the lower product outflow stream ($F_3$) in the distillation column 100 is 50 wt % or more, 80 wt % or more, 90 wt % or more, 95 wt % or more, or 99 wt % or more. In the present specification, the low boiling point stream and the upper product outflow stream ($F_2$) may be interchangeably used, and the high boiling point stream and the lower product outflow stream ($F_3$) of the distillation column 100 may be interchangeably used.

The number of theoretical plates of the distillation column 100 may be 30 to 80, 40 to 70, 25 to 50, or 45 to 60, but the number may be adjusted to various ranges according to the component to be separated, and thus is not particularly limited thereto. In addition, in this case, the raw material inflow part 121 of the distillation column 100 may be disposed at the middle part area or middle plate 120 of the distillation column 100, for example, fifth to thirtieth plate, fifth to twenty fifth plate, fifth to fifteenth plate, or tenth to twentieth plate of the distillation column 100, and this is a relative position based on the number of theoretical plates of the distillation column, and may vary depending on the number of theoretical plates of the distillation column. The "number of theoretical plates" as described above refers to the number of virtual areas or plates in which two phases such as the gas phase and the liquid phase are in equilibrium with each other in a separation process using a distillation device including the distillation column 100 and a second distillation column 200.

In an example, the upper plate outflow part 111 and the upper reflux inflow part 112 of the distillation column 100 may be disposed at the upper part 110 of the distillation column, and the upper plate outflow part 111 may be disposed at the column top of the distillation column 100. Furthermore, the lower plate outflow part 131 and the lower reflux inflow part 132 of the distillation column 100 may be disposed at the lower part 130 of the distillation column, and the lower plate outflow part 131 may be disposed at the column bottom of the distillation column 100. The "column top" as described above refers to the highest top part of the distillation column, and may be disposed at the upper plate of the above-described distillation column, and the "column bottom" as described above refers to the lowest bottom part, and may be disposed at the lower plate of the above-described distillation column. For example, the upper plate outflow part 111 of the distillation column 100 may be disposed at the column top of the distillation column 100, and the upper reflux inflow part 112 of the distillation column 100 may be disposed at the uppermost plate of the distillation column 100, for example, the first plate of the distillation column 100. Further, the lower plate outflow part 131 of the distillation column 100 may be disposed at the column bottom of the distillation column 100, and the lower reflux inflow part 132 of the distillation column 100 may be disposed at the lowermost plate of the distillation column 100, for example, the 80th plate, 70th plate, or 60th plate of the distillation column 100.

In an example, in order to perform the process of separating three components having a low boiling point, an intermediate boiling point, and a high boiling point from a raw material ($F_1$) including the three components, respectively, the raw material ($F_1$) may be introduced into the raw material inflow part 121 of the distillation column 100 as illustrated in FIG. 1. When the raw material ($F_1$) is introduced into the distillation column 100, the low boiling point stream having a relatively low boiling point among the components included in the raw material ($F_1$) may be discharged from the upper plate outflow part 111, and the intermediate boiling point stream and high boiling point stream may be discharged from the first lower plate outflow part 131. In an example, when the raw material ($F_1$) including the low boiling point, intermediate boiling point, and high boiling point components is introduced into the raw material inflow part 121 of the distillation column 100, the low boiling point component among the components of the raw material ($F_1$) flows out to the upper product outflow stream ($F_2$), the discharged upper product outflow stream ($F_2$) passes through the condenser 101, a part thereof may flow back to the upper reflux inflow part 112 of the distillation column 100, and the other parts thereof may be stored as a product. Meanwhile, the intermediate boiling point and high boiling point components among the components of the raw material ($F_1$) flow out to the lower product outflow stream ($F_3$), and the discharged lower product outflow stream ($F_3$) passes through the reboiler 102, a part thereof may flow back to the lower reflux inflow part 132 of the distillation column 100, and the other parts thereof may be produced as a product.

In an exemplary embodiment, one or more of the raw material inflow part 121, the upper reflux inflow part 112, and the lower reflux inflow part 132 of the distillation column 100 is formed of two or more openings disposed to be separated from each other. Accordingly, channeling occurring during the purification process of the raw material ($F_1$) may be blocked, thereby minimizing energy loss and enhancing the economic efficiency of the process.

In an example, the two or more openings may be disposed such that a stream introduced into or discharged from the distillation column 100 may be introduced in two or more directions or discharged in two or more directions.

In an exemplary embodiment, the distillation column 100 may include two or more small areas which equally divide a horizontal cross section. FIG. 2 is a view illustrating the cross section of the exemplary distillation column 100, which is in parallel with the ground surface. As illustrated in FIG. 2, the distillation column 100 may include any small area which divides the horizontal cross section of the distillation column 100 into an equal area, for example, a plurality of small areas ($A_{1-1}$, $A_{1-2}$, $A_{1-3}$, and $A_{1-4}$).

In an example, one or more of the raw material inflow part 121, the upper reflux inflow part 112, and the lower reflux inflow part 132 of the distillation column 100 is formed of two or more openings disposed to be separated from each other, and the two or more openings may be each disposed in two or more small areas which equally divide the horizontal cross section of the distillation column 100. The fact that the two or more openings "may be each disposed" as described above may mean that in the areas which are divided as equally as the number of the openings, one opening may be each disposed in one area. FIG. 3 is a view exemplarily illustrating the cross section of the distillation column 100 in which two or more openings are formed according to the present application, which is in parallel with the ground surface. For example, as divided by a virtual dotted line in FIG. 3, the cross section of the distillation column 100 may be divided into two equal small areas ($A_{1-1}$ and $A_{1-2}$), and when one or more of the raw material inflow part 121, the upper reflux inflow part 112, and the lower reflux inflow part 132 is formed of two openings disposed to be separated from each other, one of the two openings is disposed at one small area ($A_{1-1}$) and the other is disposed at the other small area ($A_{1-2}$), which is adjacent to the area in which the one opening is disposed, thereby disposing each one opening at each area.

In the case of a distillation column in which the raw material inflow part 121, the upper reflux inflow part 112, and the lower reflux inflow part 132 is formed of one opening, a raw material or reflux stream is supplied in only one direction, and in this case, channeling may occur. However, when one or more of the raw material inflow part 121, the upper reflux inflow part 112, and the lower reflux inflow part 132 of the distillation column 100 is formed of two or more openings, the raw material ($F_1$) and the reflux stream may be equally introduced in two or more directions, thereby preventing the channeling from occurring.

In the distillation column 100 according to the present application, channeling may be effectively suppressed by controlling the position of each opening and the flow rate and direction of a stream introduced into or discharged from each opening depending on the number of two or more openings.

In an example, the distillation column 100 in which one or more of the raw material inflow part 121, the upper reflux inflow part 112, and the lower reflux inflow part 132 is formed of two or more openings may satisfy the following Equation 1. When the distillation column 100 including two or more inflow parts satisfying the following Equation 1 is used, channeling may be minimized from occurring, and accordingly, the amount of energy consumed may be reduced, and the raw material 110 may be separated with high efficiency.

$$-5° \leq \Delta\theta \leq 5°$$ [Equation 1]

In Equation 1, $\Delta\theta$ denotes a difference between two angles which an extension line extending from any one of the two or more openings to the center of the distillation column 100 and an extension line extending from one or two openings adjacent to the one opening to the center of the distillation column 100 form.

For example, when one or more of the raw material inflow part 121, the upper reflux inflow part 112, and the lower reflux inflow part 132 of the distillation column 100 is formed of two openings disposed to be separated from each other, the two openings may be each disposed in the two small areas ($A_{1-1}$ and $A_{1-2}$) which equally divide the cross section of the distillation column 100, which is in parallel with the ground surface, as described above. Specifically, as illustrated in FIG. 4, the two openings may be disposed in opposite sides with respect to the central point of the cross section, and the raw material ($F_1$) may be each introduced into the two raw material inflow parts 121, so that it is possible to efficiently suppress channeling generated while the raw material ($F_1$) is introduced. In an example, as in FIG. 4, when one or more of the raw material inflow part 121, the upper reflux inflow part 112, and the lower reflux inflow part 132 is formed of two openings disposed to be separated from each other, an extension line ($L_1$) extending from one of the two openings to the center of the distillation column and an extension line ($L_2$) extending from the other opening to the center of the distillation column form two angles ($\theta_1$ and $\theta_2$), and $\Delta\theta$ ($\theta_1$-$\theta_2$), which is a difference between the two angles, may satisfy −5° to 5°. Further, in this case, the angle, which the extension line ($L_1$) extending from any one of the two openings to the center of the distillation column and the extension line ($L_2$) extending from the other opening to the center of the distillation column form, may be, for example, 175° to 185°, 177° to 183°, or 179° to 181° as in FIG. 4, and channeling may be minimized from occurring by controlling the angle to the range. In an example, when the two openings are completely symmetric with each other, that is, the extension line ($L_1$) extending from any one of the two openings to the center of the distillation column and the extension line ($L_2$) extending from the other opening to the center of the distillation column are on the same line, $\Delta\theta$ ($\theta_1$-$\theta_2$) may be 0°.

As illustrated in FIG. 5, one or more of the raw material inflow part 121, the upper reflux inflow part 112, and the lower reflux inflow part 132 of the distillation column 100 is formed of three openings disposed to be separated from each other, the three openings may be each disposed in the three small areas ($A_{1-1}$, $A_{1-2}$, and $A_{1-3}$), which equally divide the cross section of the distillation column 100, which is in parallel with the ground surface. Specifically, as illustrated in FIG. 6, the three openings may be disposed at certain intervals, and may be disposed such that the stream of fluid may be each introduced into or discharged from the three openings. In an example, when one or more of the raw material inflow part 121, the upper reflux inflow part 112, and the lower reflux inflow part 132 is formed of three openings disposed to be separated from each other, an extension line ($L_1$) extending from one of the three openings to the center of the distillation column and extension lines ($L_2$ and $L_3$) each extending from the other two openings to the center of the distillation column form two angles ($\theta_1$ and $\theta_2$), and $\triangle\theta$ ($\theta_1$-$\theta_2$), which is a difference between the two angles, may satisfy −5° to 5°. Furthermore, in this case, the angle, which the extension line ($L_1$) extending from any one of the three openings to the center of the distillation column and the extension lines ($L_2$ and $L_3$) each extending from the other two openings to the center of the distillation column form, may be, for example, 115° to 125°, 117° to 123°, or 119° to 121° as in FIG. 6, and channeling may be minimized from occurring by controlling the angle to the range. In an example, when the three openings are disposed at an equal interval at the outer circumferential surface of the distillation column, that is, the angle, which the extension line ($L_1$) extending from any one of the three openings to the center of the distillation column and the extension lines ($L_2$ and $L_3$) extending from the other two openings to the center of the distillation column form, is 120°, $\triangle\theta$ ($\theta_1$-$\theta_2$) may be 0°.

As in FIG. 7, one or more of the raw material inflow part 121, the upper reflux inflow part 112, and the lower reflux inflow part 132 of the distillation column 100 is formed of four openings disposed to be separated from each other, the four openings may be each disposed in the four small areas ($A_{1-1}$, $A_{1-2}$, $A_{1-3}$, and $A_{1-4}$), which equally divide the cross section of the distillation column 100, which is in parallel with the ground surface. Specifically, as illustrated in FIG. 8, the four openings may be disposed at certain intervals, and may be disposed such that the stream of fluid may be each introduced into or discharged from the four openings. In an example, when one or more of the raw material inflow part 121, the upper reflux inflow part 112, and the lower reflux inflow part 132 is formed of four openings disposed to be separated from each other, an extension line ($L_1$) extending from one of the four openings to the center of the distillation column and extension lines ($L_2$ and $L_3$) each extending from two openings adjacent to the one opening to the center of the distillation column form two angles ($\theta_1$ and $\theta_2$), and $\triangle\theta$ ($\theta_1$-$\theta_2$), which is a difference between the two angles, may satisfy −5° to 5°. Further, in this case, the angle, which the extension line ($L_1$) extending from any one of the four openings to the center of the distillation column and the extension lines ($L_2$ and $L_3$) each extending from the two openings adjacent to the one opening to the center of the distillation column form, may be, for example, 85° to 95°, 87° to 93°, or 89° to 91° as in FIG. 7, and channeling may be minimized from occurring by controlling the angle to the range. In an example, when the four openings are disposed at an equal interval at the outer circumferential surface of the distillation column, that is, the angle, which the extension line ($L_1$) extending from any one of the four openings to the center of the distillation column and the extension lines ($L_2$ and $L_3$) extending from the two openings adjacent to the one opening to the center of the distillation column form, is 90°, $\triangle\theta$ ($\theta_1$-$\theta_2$) may be 0°.

When the stream of fluid introduced into or discharged from the distillation column 100 is supplied or discharged in two or more directions, it is possible to uniformly maintain the stream of a liquid to drop onto the lower part area of plates at which the raw material inflow part 121, the upper reflux inflow part 112, and the lower reflux inflow part 132 of the distillation column 100 are disposed, thereby enhancing the purification efficiency. That is, when the raw material inflow part 121, the upper reflux inflow part 112, and the lower reflux inflow part 132 of the distillation column 100, in which two or more openings are formed, satisfy the aforementioned conditions, it is possible to effectively block channeling generated while each stream is introduced, and the design and operation convenience of the distillation device are excellent, so that the raw material ($F_{1-1}$) may be separated with high efficiency.

As illustrated in FIGS. 4, 6, and 8, the distillation column 100 of the present application may allow all the vector components of the inflow speed projected onto the cross section of the distillation column 100, which is in parallel with the ground surface to be directed toward the central point of the cross section. Specifically, the dimensions of the flow rate and the inflow speed to be introduced through the two or more openings are the same as each other, and a value obtained by each adding up the products of the flow rate (F) of the stream of fluid and the vector component of the inflow speed projected onto the cross section may be 0 (zero). As described above, when each of the sums of the products of the flow rate of the stream of fluid and the vector component of the inflow speed projected onto the cross section through two or more openings is offset to 0 (zero), channeling due to the stream of two or more fluids may be effectively blocked. The term "flow rate (F)" as described above refers to a flow rate (volume per unit time) to be introduced through each inflow part, and the term "vector component of the inflow speed" refers to a vector component in which the vector of the inflow speed (distance per unit time) through each inflow part is projected onto the cross section of the distillation column, which is in parallel with the ground surface.

In an example, the distillation column 100 in which one or more of the raw material inflow part 121, the upper reflux inflow part 112, and the lower reflux inflow part 132 is formed of two openings disposed to be separated from each other may satisfy the following Equation 2, and accordingly, it is possible to minimize the occurrence of channeling.

$$F_1 \times V_1 + F_2 \times V_2 = 0 \quad \text{[Equation 2]}$$

In Equation 2, $F_1$ and $F_2$ denote a flow rate (volume per unit time) to be introduced through each inflow part, and $V_1$ and $V_2$ denote a vector component in which the vector of the inflow speed (distance per unit time) through each inflow part is projected onto the cross section of the distillation column 100, which is in parallel with the ground surface.

In addition, the distillation column 100 in which one or more of the raw material inflow part 121, the upper reflux inflow part 112, and the lower reflux inflow part 132 is formed of three openings disposed to be separated from each other may satisfy the following Equation 3, and accordingly, it is possible to minimize the occurrence of channeling.

$$F_1 \times V_1 + F_2 \times V_2 + F_3 \times V_3 = 0 \quad \text{[Equation 3]}$$

In Equation 3, $F_1$, $F_2$, and $F_3$ denote a flow rate (volume per unit time) to be introduced through each inflow part, and $V_1$, $V_2$, and $V_3$ denote a vector component in which the vector of the inflow speed (distance per unit time) through each inflow part is projected onto the cross section of the distillation column 100, which is in parallel with the ground surface.

The distillation column 100 in which one or more of the raw material inflow part 121, the upper reflux inflow part 112, and the lower reflux inflow part 132 is formed of four openings disposed to be separated from each other may satisfy the following Equation 4, and accordingly, it is possible to minimize the occurrence of channeling.

$$F_1 \times V_1 + F_2 \times V_2 + F_3 \times V_3 + F_4 \times V_4 = 0 \qquad \text{[Equation 4]}$$

In Equation 4, $F_1$, $F_2$, $F_3$, and $F_4$ denote a flow rate (volume per unit time) to be introduced through each inflow part, and $V_1$, $V_2$, $V_3$, and $V_4$ denote a vector component in which the vector of the inflow speed (distance per unit time) through each inflow part is projected onto the cross section of the distillation column, which is in parallel with the ground surface.

In one exemplary embodiment, the raw material inflow part 121 of the distillation column 100 is formed of two or more openings disposed to be separated from each other, and the two or more openings may be each disposed at two or more middle part small areas which equally divide the cross section of the distillation column 100, which is in parallel with the ground surface. In the case of a distillation column in which the raw material inflow part 121 is formed of one opening, a liquid stream, which drops onto a lower part area of the supply plate, does not evenly drop, and channeling may occur, and accordingly, the separation efficiency of the raw material ($F_1$) may deteriorate. However, when the raw material inflow part 121 of the distillation column 100 is formed of two or more openings, channeling is suppressed by equally maintaining the stream of the liquid which drops onto the lower part of the raw material supply plate of the distillation column 100, so that the raw material ($F_1$) may be efficiently separated. In this case, the two or more openings may be disposed at the same plate inside of the distillation column 100, preferably, on the same plane in parallel with the ground surface. Accordingly, the raw material ($F_1$) to be each introduced into the two or more openings may be introduced such that a hydraulically smooth stream is obtained, thereby effectively preventing channeling. For example, the two or more raw material inflow parts 121 may be disposed at the same plate of the distillation column 100, and in the case of a distillation column 100 in which the number of theoretical plates is 30 to 80, 40 to 70, or 45 to 60, the raw material inflow part 121 which forms the two or more openings may be disposed at fifth to thirtieth plate, fifth to twenty fifth plate, or tenth to twentieth plate of the distillation column 100. Furthermore, when the raw material ($F_1$) is each introduced into the raw material inflow part 121 in which two or more openings are formed at the same flow rate, channeling is easily blocked and the operation convenience of the distillation column is excellent, so that the raw material ($F_1$) may be separated with high efficiency. Further, the raw material may be introduced into the raw material inflow part in which the two or more openings are formed at the same flow rate, and accordingly, it is possible to minimize the occurrence of channeling.

In another exemplary embodiment, the upper reflux inflow part 112 of the distillation column 100 is formed of two or more openings disposed to be separated from each other, and the two or more openings may be each disposed at two or more upper part small areas which equally divide the cross section, that is, the horizontal cross section, of the distillation column 100, which is in parallel with the ground surface. In the distillation column 100 in which the upper reflux inflow part 112 is formed of one opening, channeling may occur while the reflux stream of the upper product outflow stream ($F_2$) is introduced into the distillation column 100 in one direction. Accordingly, the separation efficiency of the raw material ($F_1$) may deteriorate, and in this case, additional energy is consumed in order to maintain the concentration of the low boiling point component in the upper product outflow stream ($F_2$). However, when the upper reflux inflow part 112 of the distillation column 100 is formed of two or more openings, the reflux stream of the upper product outflow stream ($F_2$) is introduced into the distillation column in two or more directions, and thus, channeling is suppressed, thereby efficiently separating the raw material ($F_1$). In an example, the two or more upper reflux inflow parts 112 may be disposed on the same plate in the upper plate of the distillation column 100, preferably, on the same plane in parallel with the ground surface, and in the case of a distillation column 100 in which the number of theoretical plates is 30 to 80, 40 to 70, or 45 to 60, the upper reflux inflow part 112 in which the two or more openings are formed may be disposed at the uppermost plate, for example, the first plate of the distillation column 100.

In addition, the lower reflux inflow part 132 of the distillation column 100 is formed of two or more openings disposed to be separated from each other, and the two or more openings may be each disposed at two or more lower part small areas which equally divide the horizontal cross section of the distillation column 100. In this case, the lower product outflow stream ($F_3$) which has passed through the reboiler 102 may flow back in two or more directions, thereby enhancing the separation efficiency of the raw material ($F_1$). For example, the lower reflux inflow part 132 in which the two or more openings are formed may be disposed on the same plate in the lower plate of the distillation column 100, preferably, on the same plane in parallel with the ground surface, and in the case of a distillation column 100 in which the number of theoretical plates is 30 to 80, 40 to 70, or 45 to 60, the lower reflux inflow part 132 in which the two or more openings are formed may be disposed at the lowermost plate, for example, the eightieth plate, the seventieth plate, or the sixtieth plate, of the distillation column 100.

In another exemplary embodiment, all of the raw material inflow part 121, the upper reflux inflow part 112, and the lower reflux inflow part 132 of the distillation column 100 are formed of two or more openings disposed to be separated from each other, and in this case, the raw material may be each introduced into the raw material inflow part 121 in which the two or more openings are formed, a part of the upper product outflow stream ($F_2$) may be each introduced into the upper reflux inflow part 112 in which the two or more openings are formed, and a part of the lower product outflow stream ($F_3$) may be each introduced into the lower reflux inflow part 132 in which two or more openings are formed.

For example, the raw material inflow part 121 in which the two or more openings are formed may be each disposed in two or more middle part small areas which equally divide the cross section of the distillation column 100, which is in parallel with the ground surface. In this case, the two or more openings may be disposed at the same plate inside of the distillation column 100, preferably, on the same plane in parallel with the ground surface, the upper reflux inflow part 112 in which the two or more openings are formed may be each disposed on the cross section of the distillation column 100, which is in parallel with the ground surface, that is, two or more upper part small areas which equally divide the horizontal cross section, and in addition, the lower reflux inflow part 132 in which the two or more openings are formed may be each disposed in two or more lower part small areas which equally divide the horizontal cross section of the distillation column 100. In this case, the two or more raw material inflow parts 121 may be disposed at the same plate of the distillation column 100, the two or more upper reflux inflow parts 112 may be disposed at the same plate in the upper plate of the distillation column 100, preferably, on the same plane in parallel with the ground surface, and the lower reflux inflow part 132 in which the two or more openings are formed may be disposed at the same plate in the lower plate of the distillation column 100, preferably on the same plane in parallel with the ground surface. The description on the specific plates of the raw material inflow part, the upper reflux inflow part 112, and the lower reflux inflow part 132 is the same as that described above, and thus, will be omitted. Furthermore, as described above, the raw material to be each introduced into the raw material inflow part in which the two or more openings are formed may be introduced at the same flow rate, the reflux stream to be each introduced into the upper reflux inflow part in which the two or more openings are formed may be introduced at the same flow rate, and the reflux stream to be each introduced into the lower reflux inflow part in which the two or more openings are formed may be introduced at the same flow rate, and accordingly, it is possible to minimize the occurrence of channeling.

Specific contents on the raw material inflow part 121, the upper reflux inflow part 112, and the lower reflux inflow part 132 in which the two or more openings are formed are the same as those described above, and thus, will be omitted.

FIG. 9 is a view exemplarily illustrating the distillation device according to another exemplary embodiment of the present application.

The distillation device according to an exemplary embodiment of the present application includes a condenser 201 and a reboiler 202, and may include a dividing wall distillation column 200 including a dividing wall 203 inside of the distillation column.

As illustrated in FIG. 9, the distillation column 200 included in the distillation device may be a dividing wall distillation column 200 including a dividing wall 203 inside of the distillation column 200. The dividing wall distillation column 200 is a device designed to distill a raw material ($F_1$) including three components having a low boiling point, an intermediate boiling point, and a high boiling point, and a device similar to a so-called thermally coupled distillation column (Petlyuk column) from the thermodynamic viewpoint. The thermally coupled distillation column is designed to primarily separate low boiling point and high boiling point materials from a preliminary separator, and separate each of low boiling point, intermediate boiling point, and high boiling point materials from a main separator. In this regard, the dividing wall distillation column 200 is a type in which the preliminary separator is integrated into the main separator by disposing the dividing wall 203 inside of the column.

For example, the inside of the distillation column 200 is divided by the dividing wall 203, and as divided by virtual dotted lines in the drawing, the inside of the distillation column 200 may be divided into a middle part area divided by the dividing wall 203, and an upper part area 210 and a lower part area 240 in which the dividing wall is not disposed. Furthermore, the middle part area may be divided into a first middle part area 220 and a second middle part area 230 divided by the dividing wall 203. Accordingly, the inside of the distillation column 200 may be divided into the upper part area 210, the lower part area 240, and the middle part area, and further, the middle part area may be divided into the first middle part area 220 and the second middle part area 230. In the dividing wall distillation column of the present application, the first middle part area 220 and the second middle part area 230 are separated from or isolated from each other by the dividing wall 203. Accordingly, the stream inside of the first middle part area 220 and the stream inside of the second middle part area 230 may be prevented from being mixed with each other. The term "separated from or isolated from" in the present specification means that the stream in each area flows or is present independently from the area separated by the dividing wall 203.

In an example, the dividing wall 203 disposed inside of the distillation column 200 may be disposed in the middle part area. Specifically, the length of the dividing wall 203, when calculated based on the number of theoretical plates of the distillation column 200, may be a length corresponding to the number of plates of 40% or more of the total number of theoretical plates, for example, a length corresponding to the number of plates of 50% or more, or 60% or more of the total number of theoretical plates. The dividing wall 203 of the distillation column 200 may be disposed inside of the distillation column 200 at a length in the range, thereby effectively blocking the stream inside of the first middle part area 220 and the stream inside of the second middle part area 230 from being mixed. Further, low boiling point components in the stream discharged from a product outflow part 231 may be prevented from being mixed and discharged.

In an example, a raw material inflow part 221 of the distillation column 200 may be disposed in the first middle part area 220 of the distillation column 200. Further, an upper plate outflow part 211 and an upper reflux inflow part 212 may be disposed in the upper part area 210 of the distillation column 200, and preferably, the upper plate outflow part 211 may be disposed at the column top inside of the upper part area 210 of the distillation column 200. In addition, a lower plate outflow part 241 and a lower reflux inflow part 242 may be disposed in the lower part area 240 of the distillation column 200, and preferably, the lower plate outflow part 241 may be disposed at the column bottom inside of the lower part area 240 of the distillation column 200. Furthermore, the distillation column includes the product outflow part 231, and the product outflow part 231 may be disposed at the second middle part area 230 of the distillation column 200.

In an example, in order to perform the process of separating three components having a low boiling point, an intermediate boiling point, and a high boiling point from a raw material ($F_1$) including the three components, respectively, the raw material ($F_1$) may be introduced into the first middle part area 220 of the distillation column 200 as illustrated in FIG. 9. In an example, the raw material ($F_1$) is introduced into the raw material inflow part 221 in the first middle part area 220 of the distillation column 200, a low boiling point stream having a relatively low boiling point among the components included in the raw material ($F_1$) is introduced into the upper part area 210, and an intermediate boiling point stream and a high boiling point stream each having a relatively high boiling point are introduced into the lower part area 240. Further, the low boiling point stream introduced into the upper part area 210 is discharged from the upper plate outflow part 211 to the upper product outflow stream ($F_2$) and passes through the condenser 201, and then a part thereof flows back to the upper reflux inflow part 212 of the distillation column 200, or is stored as a product. In addition, the high boiling point stream introduced into the lower part area 240 is discharged from the lower plate outflow part 241 to the lower product outflow stream ($F_3$) and passes through the reboiler 202, and then a part thereof flows back to the lower reflux inflow part 242 of the distillation column 200, or is stored as a product. A stream of a component having a relatively high boiling point in the stream introduced into the upper part area 210 and a stream of a component having a relatively low boiling point in the stream introduced into the lower part area 240, that is, the intermediate boiling point stream is introduced into the second middle part area 230, and may be discharged from the product outflow part 231 of the second middle part area 230. The term "intermediate boiling point stream" refers to a stream which is rich in a component having a boiling point between a low boiling point component and a high boiling point component in a raw material flow including three components having a low boiling point, an intermediate boiling point, and a high boiling point, and the intermediate boiling point stream refers to, for example, a stream discharged from the product outflow part 231 of the distillation column 200.

In an exemplary embodiment of the present application, one or more of the raw material inflow part 221 and the product outflow part 231 of the dividing wall distillation column 200 is formed of two or more openings disposed to be separated from each other. Accordingly, channeling occurring during the purification process of the raw material ($F_1$) may be blocked, thereby minimizing energy loss and enhancing the economic efficiency of the process.

In an example, the two or more openings may be disposed such that a stream introduced into or discharged from the dividing wall distillation column 200 may be introduced in two or more directions or discharged in two or more directions. For example, the first middle part area 220 of the dividing wall distillation column 200 may include two or more first middle part small areas which equally divide the horizontal cross section of the distillation column 200. FIG. 10 is a view illustrating the cross section of the middle part area of the exemplary dividing wall distillation column 200, which is in parallel with the ground surface. As illustrated in FIG. 10, the middle part area of the dividing wall distillation column 200 is divided into the first middle part area 220 and the second middle part area 230 by the dividing wall 203, the first middle part area 220 includes any small area which divides the horizontal cross section of the distillation column 200 into an equal area, for example, a plurality of first middle part small areas 220a and 220b, and the second middle part area 230 may similarly include any plurality of second middle part small areas 230a and 230b which divide the horizontal cross section of the distillation column 200 into an equal area. Preferably, the first middle part small areas 220a and 220b and the second middle part small areas 230a and 230b may be each a area which divides the horizontal cross section of the first middle part area 220 and the second middle part area 230 into an equal area.

In an example, the raw material inflow part 221 of the first middle part area 220 and/or the product outflow part 231 of the second middle part area 230 of the dividing wall distillation column 200 are/is formed of two or more openings, and in this case, the raw material inflow part 221 in which the two or more openings are formed is disposed in the two or more first middle part small areas, respectively, and the product outflow part 231 in which the two or more openings are formed may be disposed in the two or more second middle part small areas, respectively. FIG. 11 is a view exemplarily illustrating the cross section of the middle part area of the dividing wall distillation column 200 in which two or more openings are formed according to the present application, which is in parallel with the ground surface. For example, as divided by virtual dotted lines in FIG. 11, the first middle part area 220 may include two equally divided first middle part small areas 220a and 220b, and when the raw material inflow part 221 of the dividing wall distillation column 200 is formed of two openings disposed to be separated from each other, one opening may be disposed in one middle part small area 220a of the two first middle part small areas 220a and 220b and the other opening may be disposed in the other middle part small area 220b adjacent to the middle part small area 220a in which the one opening is disposed, thereby disposing one opening in each area.

In the case of the dividing wall distillation column 200 in which the raw material inflow part 221 is formed of one opening, the raw material ($F_1$) is supplied in one direction only, and in this case, channeling may occur. However, when the raw material inflow part 221 of the dividing wall distillation column 200 is formed of two or more openings, the raw material ($F_1$) may be equally introduced in two or more directions, thereby preventing the channeling.

In the dividing wall distillation column 200 according to the present application, channeling may be effectively suppressed by controlling the position of each opening and the flow rate and direction of each stream depending on the number of two or more openings. For example, when the raw material inflow part 221 of the dividing wall distillation column 200 is formed of two openings, the two raw material inflow parts 221 may be each disposed in the first middle part small areas 220a and 220b, which equally divide the cross section of the first middle part area 220, which is in parallel with the ground surface into two parts, as described above. In this case, an angle, which an extension line extending from any one of the two openings to the center of the distillation column 200 and an extension line extending from the other opening to the center of the distillation column 200 form, may be 85° to 95°, 87° to 93°, or 89° to 91°, and blocking of channeling may be maximized by controlling the angle to the range. Further, in this case, all the directions of the vector components of each raw material ($F_1$) stream introduced through the two raw material inflow parts 221 may be directed toward the central point of the cross section of the dividing wall distillation column 200, which is in parallel with the ground surface, and for example, the vector components of the inflow speed projected onto the cross section of each raw material flow may be symmetric with each other based on the a surface 2031 vertical to the dividing wall 203, which passes through the central point of the cross section of the dividing wall-type distillation column 200, which is in parallel with the ground surface.

FIG. 12 is a view exemplarily illustrating the cross section of the middle part area of the dividing wall distillation column 200 in which three openings are formed according to the present application, which is in parallel with the ground surface. As in FIG. 12, for example, the raw material inflow part 221 of the dividing wall distillation column 200 is formed of three openings disposed to be separated from each other, and the three openings may be each disposed in the first middle part small areas 220a, 220b, and 220c, which equally divide the cross section of the first middle part area 220, which is in parallel with the ground surface into three parts. In this case, an angle, which an extension line extending from any one of the three openings of the dividing wall distillation column 200 to the center of the distillation column 200 and an extension line extending from openings adjacent to the one opening to the center of the distillation column 200 form, may be 55° to 65°, 57° to 63°, or 59° to 61°, and blocking of channeling may be maximized by controlling the angle to the range. In addition, in this case, channeling may be substantially blocked from occurring by equally controlling the flow rate and inflow speed of each of streams introduced from the three openings.

FIG. 13 is a view exemplarily illustrating the cross section of the dividing wall distillation column 200 in which four openings are formed, which is in parallel with the ground surface. As illustrated in FIG. 13, for example, the raw material inflow part 221 of the dividing wall distillation column 200 is formed of four openings disposed to be separated from each other, and the four openings may be each disposed in the first middle part small areas 220a, 220b, 220c, and 220d, which equally divide the cross section of the first middle part area 220, which is in parallel with the ground surface into four parts. In this case, an angle, which an extension line extending from any one of the four openings of the dividing wall distillation column 200 to the center of the distillation column 200 and an extension line extending from openings adjacent to the one opening to the center of the distillation column 200 form, may be 40° to 50°, 42° to 48°, or 44° to 46°, and blocking of channeling may be maximized by controlling the angle to the range. Furthermore, in this case, channeling may be substantially blocked from occurring by equally controlling the flow rate and inflow speed of each of streams introduced from the four openings.

In an exemplary embodiment, the raw material inflow part 221 of the dividing wall distillation column 200 is formed of two or more openings disposed to be separated from each other, and the two or more openings may be each disposed in two or more first middle part small areas, which equally divide the cross section of the dividing wall distillation column 200, which is in parallel with the ground surface, preferably, which divide the horizontal cross section of the first middle part area 220 into an equal area. In the case of a dividing wall distillation column 200 in which the raw material inflow part 221 is formed of one opening, a liquid stream, which drops onto a lower part area of the supply plate of the dividing wall distillation column, does not evenly drop, and channeling may occur, and accordingly, the separation efficiency of the raw material ($F_1$) may deteriorate. However, when the raw material inflow part 221 of the dividing wall distillation column 200 is formed of two or more openings, it is possible to evenly maintain the stream of the liquid which drops onto the lower part of the raw material supply plate of the dividing wall distillation column 200 and channeling is suppressed, so that the raw material ($F_1$) may be efficiently separated. In this case, the two or more openings may be disposed at the same plate inside of the first middle part area 220. Accordingly, the raw material ($F_1$) to be each introduced into the two or more openings may be introduced such that a hydraulically smooth stream is obtained, thereby effectively preventing channeling. For example, the two or more raw material inflow parts 221 may be disposed at the same plate inside of the first middle part area 220 of the dividing wall distillation column 200, preferably, on the same plane in parallel with the ground surface, and in the case of a dividing wall distillation column 200 in which the number of theoretical plates is 30 to 80, 40 to 70, or 45 to 60, the raw material inflow part 221 which forms the two or more openings may be disposed at fifth to thirtieth plate, fifth to twenty fifth plate, or tenth to twentieth plate of the dividing wall distillation column 200. Further, when the raw material ($F_1$) is each introduced into the raw material inflow part 221 in which two or more openings are formed at the same flow rate, channeling is easily blocked and the operation convenience of the distillation column is excellent, so that the raw material ($F_1$) may be separated with high efficiency.

According to anther exemplary embodiment of the present application, the second middle part area 230 of the dividing wall distillation column 200 may include a plurality of second middle part small areas, which divide the horizontal cross section of the distillation column 200 into an equal area, preferably, divide the horizontal cross section of the second middle part area 230 into an equal area. At this time, the product outflow part 231 of the dividing wall column 200 is formed of two or more openings disposed to be separated from each other, and the two or more openings may be each disposed in the two or more second middle part small areas. FIG. 14 is a view exemplarily illustrating the cross section of the dividing wall distillation column 200 in which two openings are formed, which is in parallel with the ground surface. For example, as divided by virtual dotted lines in FIG. 14, the second middle part area 230 may include two equally divided second middle part small areas 230a and 230b, and when the product outflow part 231 of the dividing wall distillation column 200 is formed of two openings disposed to be separated from each other, one opening may be disposed in one middle part small area 230a of the two second middle part small areas 230a and 230b and the other opening may be disposed in the other middle part small area 230b adjacent to the middle part small area 230a in which the one opening is disposed, thereby disposing one opening in each area. In the case of the dividing wall distillation column 200 in which the product outflow part 231 is formed of one opening, the product is discharged in one direction only, and in this case, channeling may occur. Accordingly, the separation efficiency of the raw material ($F_1$) may deteriorate, and in this case, additional energy is consumed in order to maintain the concentration of the intermediate boiling point component in the product outflow stream ($F_4$). However, when the product outflow part 231 of the dividing wall distillation column 200 is formed of two or more openings, the product outflow stream may be equally discharged in two or more directions, thereby preventing the channeling.

In an example, the two or more product outflow parts 231 may be disposed in the same plate inside of the second middle part area 230 of the dividing wall distillation column 200, preferably, on the same plane in parallel with the ground surface. For example, in the case of a dividing wall distillation column 200 in which the number of theoretical plates is 30 to 80, 40 to 70, or 45 to 60, the product outflow part 231 in which the two or more openings are formed may be disposed at fifth to thirtieth plate, fifth to twenty fifth plate, or tenth to twentieth plate.

The specific contents on the product outflow part 231 are the same as that on the above-described raw material inflow part 221, and thus, will be omitted.

In an exemplary embodiment, all of the raw material inflow part 221, the upper reflux inflow part 212, the product outflow part 231, and the lower reflux inflow part 242 of the dividing wall distillation column 200 are formed of two or more openings, thereby maximizing blocking of channeling which may be generated by the reflux stream. Exemplary embodiments of the upper reflux inflow part 212 and the lower reflux inflow part 242 of the above-described dividing wall distillation column 200 may be applied to the upper plate outflow part 211 and the lower plate outflow part 241 as they are to correspond to each other, respectively. The specific contents on this are the same as described above, and thus, will be omitted.

The present application relates to a distillation method of a mixture using the above-described distillation device. In an example, the method includes: introducing a raw material into a raw material inflow part of a distillation column in which one or more of the raw material inflow part, an upper reflux inflow part, and a lower reflux inflow part is formed of two or more openings disposed to be separated from each other to distil the raw material, and accordingly, channeling may be minimized and the separation efficiency may be enhanced by the distillation method of the present application.

The distillation device of the present application may be used in various chemical industrial applications. For example, the device may be used in processes of separating mixtures such as crude oil, but is not limited thereto.

Advantageous Effects

According to the distillation device of the present application, channeling occurring during the separation of a mixture may be blocked, thereby enhancing the separation efficiency and achieving energy saving.

BRIEF DESCRIPTION OF DRAWINGS

FIG. 1 is a view exemplarily illustrating a distillation device according to exemplary embodiments of the present application.

FIG. 2 is a view illustrating the cross section of the exemplary distillation column, which is in parallel with the ground surface.

FIGS. 3 and 4 are views exemplarily illustrating the cross section of the distillation column in which two openings are formed according to the present application, which is in parallel with the ground surface.

FIGS. 5 and 6 are views exemplarily illustrating the cross section of the distillation column in which three openings are formed according to the present application, which is in parallel with the ground surface.

FIGS. 7 and 8 are views exemplarily illustrating the cross section of the distillation column in which four openings are formed according to the present application, which is in parallel with the ground surface.

FIG. 9 is a view exemplarily illustrating a distillation device according to other exemplary embodiments of the present application.

FIG. 10 is a view illustrating the cross section of the middle part area of the exemplary dividing wall distillation column, which is in parallel with the ground surface.

FIGS. 11 and 14 are views exemplarily illustrating the cross section of the middle part area of the distillation column in which two openings are formed according to the present application, which is in parallel with the ground surface.

FIG. 12 is a view exemplarily illustrating the cross section of the middle part area of the dividing wall distillation column in which three openings are formed according to the present application, which is in parallel with the ground surface.

FIG. 13 is a view exemplarily illustrating the cross section of the middle part area of the dividing wall distillation column in which four openings are formed according to the present application, which is in parallel with the ground surface.

BEST MODE

Hereinafter, the present application will be described in more detail with reference to Examples which follow the present application and Comparative Examples which do not follow the present application, but the scope of the present application is not limited by the following Examples.

EXAMPLE 1

2-Ethylhexyl acrylate was purified by using the distillation device of FIG. 1. Specifically, a raw material including 2-ethylhexyl acrylate at 20° C. to 40° C. was introduced into two raw material inflow parts disposed at the fifteenth plate of a first distillation column in which the number of theoretical plates was 60, and the flow rate of the raw material introduced into each raw material inflow part was equally controlled.

In this case, the operation pressure of the upper part of the first distillation column was maintained at about 20 to 30 torr, the operation temperature thereof was maintained at about 90 to 105° C., the operation pressure of the lower part of the first distillation column was maintained at about 80 to 90 torr, and the operation temperature was maintained at 140 to 147° C. A part of the stream discharged from the first plate of the first distillation column was allowed to pass through a condenser and flow back to the first distillation column, a part of the stream discharged from the sixtieth plate of the first distillation column was allowed to pass through a reboiler and flow back to the first distillation column, and at this time, the reflux ratio of the stream discharged from the upper plate of the first distillation column was set to be 1.5 to 4.5, and the reflux ratio of the stream discharged from the lower plate of the first distillation column was set to be 10 to 20.

EXAMPLE 2

Purification was performed in the same manner as in Example 1, except that a distillation column was used, the distillation column being formed such that two openings were each formed in a raw material inflow part and a upper reflux inflow part, the two raw material inflow parts were disposed at the fifteenth plate of a first distillation column in which the number of theoretical plates was 60, and the two upper reflux inflow parts were disposed at the first plate of the distillation column in which the number of theoretical plates was 60.

EXAMPLE 3

Purification was performed in the same manner as in Example 1, except that a distillation column was used, the distillation column being formed such that two openings were each formed in a raw material inflow part and a lower reflux inflow part, the two raw material inflow parts were disposed at the fifteenth plate of a first distillation column in which the number of theoretical plates was 60, and the two lower reflux inflow parts were disposed at the sixtieth plate of the first distillation column in which the number of theoretical plates was 60.

EXAMPLE 4

Purification was performed in the same manner as in Example 1, except that a distillation column was used, the distillation column being formed such that two openings were each formed in a raw material inflow part, a lower reflux inflow part, and an upper reflux inflow part, the two raw material inflow parts were disposed at the fifteenth plate of the distillation column in which the number of theoretical plates was 60, the two lower reflux inflow parts were disposed at the sixtieth plate of the distillation column in which the number of theoretical plates was 60, and the two upper reflux inflow parts were disposed at the first plate of the distillation column in which the number of theoretical plates was 60.

EXAMPLE 5

Purification was performed in the same manner as in Example 1, except that a dividing wall distillation column having a dividing wall as in FIG. 9 was used as a first distillation column. A raw material including 2-ethylhexyl acrylate was introduced into a raw material inflow part disposed in a first middle part area of the distillation column, in which two openings were formed, and specifically, the raw material was introduced into the fiftieth plate of the first distillation column in which the number of theoretical plates was 60.

EXAMPLE 6

Purification was performed in the same manner as in Example 5, except that a distillation column was used, the distillation column being formed such that two openings were each formed in a raw material inflow part and a product outflow part, the two raw material inflow parts were disposed in a first middle part area and at the fifteenth plate of the distillation column in which the number of theoretical plates was 60, and the two product outflow parts were disposed in a second middle part area and at the fifteenth plate of the distillation column in which the number of theoretical plates was 60.

EXAMPLE 7

Purification was performed in the same manner as in Example 1, except that a distillation column was used, in which three openings were formed in a raw material inflow part, and the three raw material inflow parts were formed as in FIG. 5.

EXAMPLE 8

Purification was performed in the same manner as in Example 1, except that a distillation column was used, in which four openings were formed in a raw material inflow part, and the four raw material inflow parts were formed as in FIG. 7.

COMPARATIVE EXAMPLE

Purification was performed in the same manner as in Example 1, except that a distillation column was used, in which each one of the raw material inflow part, the upper reflux inflow part, and the lower reflux inflow part was formed.

After the raw material was separated according to the Examples and the Comparative Example, it was determined whether channeling occurred during the separation process, and the results are shown in the following Table 1.

TABLE 1

| | Comparative Example | Example 1 | Example 2 | Example 3 | Example 4 | Example 5 | Example 6 | Example 7 | Example 8 |
|---|---|---|---|---|---|---|---|---|---|
| Occurrence of channeling | o | x | x | x | x | x | x | x | x |

* x: Channeling not occurred
* o: Channeling occurred

As shown in Table 1, it can be confirmed that when the raw material was separated according to the Comparative Example in which a distillation column was used, in which one opening was formed in the raw material inflow part, the upper reflux inflow part, and the lower reflux inflow part, channeling occurred, but in the Examples in which two or more openings were formed in one or more of the raw material inflow part, the product outflow part and, the upper reflux inflow part, and the lower reflux inflow part, channeling did not occur during the separation process of the raw material as compared to the Comparative Example.

Therefore, when the raw material is purified by the dividing wall distillation column which forms two or more of the inflow part and the outflow part of the present application, the separation efficiency of the raw material may be enhanced as compared to the distillation device according to the Comparative Example.

The invention claimed is:
1. A distillation device comprising:
  a distillation column comprising a condenser and a reboiler,
  wherein the distillation column comprises: an upper part area; a lower part area; and a middle part area between the upper part area and the lower part area,
  the middle part area comprises a raw material inflow part,
  a raw material introduced into the raw material inflow part is discharged while being divided into an upper product outflow stream and a lower product outflow stream,
  the upper product outflow stream is discharged from the upper part area, and a part of the upper product outflow stream passes through the condenser, and flows back to an upper reflux inflow part disposed in the upper part area,
  the lower product outflow stream is discharged from the lower part area, and a part of the lower product outflow stream passes through the reboiler, and flows back to a lower reflux inflow part disposed in the lower part area, and wherein the distillation column is a dividing wall distillation column comprising a dividing wall inside of the distillation column, the middle part area of the distillation column comprises a first middle part area and a second middle part area each divided by the dividing wall, and the second middle part area comprises a product outflow part, wherein one or more of the raw material inflow part, the upper reflux inflow part, and the lower reflux inflow part is formed of two or more openings disposed to be separated from each other, and the product outflow part is formed of two or more openings disposed to be separated from each other such that the two or more openings of the product outflow part are each disposed in two or more small areas which equally divide the horizontal cross-sectional area of the second middle part area, and wherein each of the two or more openings of the product outflow part are arranged to face two or more directions.

2. The device of claim 1, wherein the middle part area is divided into two or more middle part small areas which equally divide a horizontal cross section of the distillation column, the raw material inflow part is formed of two or more openings disposed to be separated from each other, and the two or more openings are each disposed in the two or more middle part small areas.

3. The device of claim 2, wherein the two or more openings are disposed at the same plate inside of the middle part area.

4. The device of claim 2, wherein the raw material inflow part is formed of two or more openings disposed to be separated from each other, and the raw material each introduced into the two or more openings is introduced at the same flow rate.

5. The device of claim 1, wherein the upper part area is divided into two or more upper part small areas which equally divide a horizontal cross section of the distillation column, the upper reflux inflow part is formed of two or more openings disposed to be separated from each other, and the two or more openings are each disposed in the two or more upper part small areas.

6. The device of claim 1, wherein the lower part area is divided into two or more lower part small areas which equally divide a horizontal cross section of the distillation column, the lower reflux inflow part is formed of two or more openings disposed to be separated from each other, and the two or more openings are each disposed in the two or more lower part small areas.

7. The device of claim 1, wherein the device satisfies the following Equation 1:

$$-5° \leq \Delta D \leq 5°$$ [Equation 1]

in Equation 1, ΔD denotes a difference between a first angle formed between a first extension line extending from a first of the two or more openings to a center of the distillation column and a second extension line extending from a second of the two or more openings to the center of the distillation column and a second angle formed between the first extension line and a third extension line extending from a third of the two or more openings to the center of the distillation column, wherein the second and third openings are adjacent to the first opening.

8. The device of claim 1, wherein one or more of the upper reflux inflow part, and the lower reflux inflow part is formed of two openings, and an angle, which an extension line extending from any one of the two openings to a center of the distillation column and an extension line extending from the other opening to the center of the distillation column form, is 175° to 185°.

9. The device of claim 1, wherein one or more of the upper reflux inflow part, and the lower reflux inflow part is formed of three openings, and an angle, which an extension line extending from any one of the three openings to a center of the distillation column and an extension line extending from the other two openings to the center of the distillation column form, is 115° to 125°.

10. The device of claim 1, wherein one or more of the upper reflux inflow part, and the lower reflux inflow part is formed of four openings, and an angle, which an extension line extending from any one of the four openings to a center of the distillation column and an extension line extending from two openings adjacent to the one opening to the center of the distillation column form, is 85° to 95°.

11. The device of claim 1, wherein the raw material inflow part, the upper reflux inflow part, and the lower reflux inflow part are formed of two or more openings disposed to be separated from each other, and the raw material is each introduced into the raw material inflow part in which the two or more openings are formed, a part of the upper product outflow stream is each introduced into the upper reflux inflow part in which the two or more openings are formed and flows back, and a part of the lower product outflow stream is each introduced into the lower reflux inflow part in which the two or more openings are formed and flows back.

12. The device of claim 11, wherein the middle part area is divided into two or more middle part small areas which equally divide a horizontal cross section of the distillation column, the upper part area is divided into two or more upper part small areas which equally divide the horizontal cross section of the distillation column, and the lower part area is divided into at least two lower part small areas which equally divide the horizontal cross section of the distillation column, and the raw material inflow part in which two or more openings are formed is each disposed in the two or more middle part small areas, the upper reflux inflow part in which two or more openings are formed is each disposed in the two or more upper part small areas, and the lower reflux inflow part in which two or more openings are formed is each disposed in the two or more lower part small areas.

13. The device of claim 11, wherein the raw material inflow part in which two or more openings are formed is disposed at the same plate inside of the middle part area, the upper reflux inflow part in which two or more openings are formed is disposed at the same plate inside of the upper part area, and the lower reflux inflow part in which two or more openings are formed is disposed at the same plate inside of the lower part area.

14. The device of claim 11, wherein the raw material each introduced into the raw material inflow part in which two or more openings are formed is introduced at the same flow rate, a reflux stream each introduced into the upper reflux inflow part in which two or more openings are formed is introduced at the same flow rate, and the reflux stream each introduced into the lower reflux inflow part in which two or more openings are formed is introduced at the same flow rate.

15. The device of claim 1, wherein the raw material inflow part and the product outflow part are formed of two or more openings.

16. The device of claim 15, wherein the two or more openings formed in the raw material inflow part are each disposed in two or more first middle part small areas which equally divide the horizontal cross section of the first middle part area.

17. The device of claim 16, wherein the raw material inflow part and/or the product outflow part are/is formed of two openings, and an angle, which an extension line extending from any one of the two openings to the center of the distillation column and an extension line extending from the other opening to the center of the distillation column form, is 85° to 95°.

18. The device of claim 16, wherein the raw material inflow part and/or the product outflow part are/is formed of three openings, and an angle, which an extension line extending from any one of the three openings to the center of the distillation column and an extension line extending from an opening adjacent to the one opening to the center of the distillation column form, is 55° to 65°.

19. The device of claim 16, wherein the raw material inflow part and/or the product outflow part are/is formed of four openings, and an angle, which an extension line extending from any one of the four openings to the center of the distillation column and an extension line extending from an opening adjacent to the one opening to the center of the distillation column form, is 40° to 50°.

20. A distillation method using the device according to claim 1, wherein the method includes: introducing a raw material into a raw material inflow part of a distillation column in which one or more of the raw material inflow part, an upper reflux inflow part, and a lower reflux inflow part to distil the raw material is formed of two or more openings disposed to be separated from each other.

* * * * *